United States Patent
Van Broekhoven et al.

(10) Patent No.: US 9,701,594 B2
(45) Date of Patent: Jul. 11, 2017

(54) HYDRODEOXYGENATION OF PYROLYSIS OIL IN PRESENCE OF ADMIXED ALCOHOL

(75) Inventors: Emanuel Hermanus Van Broekhoven, Monnickendam (NL); Ralph Klomp, Nieuw Vennep (NL); Ruben Theodoor Pronk, Jisp (NL); Leendert Arie Gerritsen, Lunteren (NL); Frans Lodewijk Plantenga, Hoevelaken (NL); Edgar Evert Steenwinkel, Baton Rouge, LA (US)

(73) Assignee: Albemarle Europe SPRL (NL)

( * ) Notice: Subject to any disclaimer, the term of this patent is extended or adjusted under 35 U.S.C. 154(b) by 0 days.

(21) Appl. No.: 13/883,089

(22) PCT Filed: Aug. 30, 2011

(86) PCT No.: PCT/EP2011/064897
§ 371 (c)(1),
(2), (4) Date: May 2, 2013

(87) PCT Pub. No.: WO2012/059256
PCT Pub. Date: May 10, 2012

(65) Prior Publication Data
US 2013/0225887 A1   Aug. 29, 2013

Related U.S. Application Data (60) Provisional application No. 61/467,023, filed on Mar. 24, 2011, provisional application No. 61/410,101, filed on Nov. 4, 2010.

(51) Int. Cl.
C07C 1/22 (2006.01)
C10G 3/00 (2006.01)
(Continued)

(52) U.S. Cl.
CPC ............ *C07C 1/22* (2013.01); *C10G 3/46* (2013.01); *C10G 3/50* (2013.01); *B01J 23/85* (2013.01);
(Continued)

(58) Field of Classification Search
CPC .... C07C 1/22; C07C 1/20; C10G 3/00; C10G 3/46; C10G 3/50; C10G 2300/1011;
(Continued)

(56) References Cited

U.S. PATENT DOCUMENTS

| 4,795,841 A | 1/1989 | Elliott et al. |
| 7,425,657 B1 | 9/2008 | Elliott et al. |

(Continued)

FOREIGN PATENT DOCUMENTS

| CN | 101171324 A | 4/2008 |
| CN | 101544910 A | 9/2009 |

(Continued)

OTHER PUBLICATIONS

Douglas C. Elliott; "Historical Developments in Hydroprocessing Bio-Oils"; Energy & Fuels; 2007; vol. 21; pp. 1792-1815; 2007 American Chemical Society; Published on Web May 2, 2007.

(Continued)

*Primary Examiner* — Prem C Singh
*Assistant Examiner* — Brandi M Doyle
(74) *Attorney, Agent, or Firm* — Nathaniel C. Dunn; Jeremy J. Kliebert; Marcy M. Hoefling (57) ABSTRACT

The present invention relates to the hydrodeoxygenation of pyrolysis oils in the presence of an alcohol.

13 Claims, 8 Drawing Sheets

(51) Int. Cl.
  *B01J 37/20* (2006.01)
  *B01J 23/85* (2006.01)
  *B01J 23/883* (2006.01)
(52) U.S. Cl.
  CPC .............. *B01J 23/883* (2013.01); *B01J 37/20* (2013.01); *C10G 2300/4006* (2013.01); *C10G 2300/4081* (2013.01); *C10G 2300/42* (2013.01); *Y02P 30/20* (2015.11)
(58) Field of Classification Search
  CPC .... C10G 2300/4006; C10G 2300/4081; C10G 2300/44; C10G 3/42; C10G 2300/42; Y02P 30/20
  USPC ....... 208/100, 135, 137, 141, 145, 264, 291; 585/240, 266, 269, 270, 310, 314, 315, 585/327
  See application file for complete search history.

(56) References Cited

U.S. PATENT DOCUMENTS

| | | | |
|---|---|---|---|
| 2008/0050792 A1 | 2/2008 | Zmierczak et al. | |
| 2010/0043278 A1* | 2/2010 | Brevoord | B01J 23/85 44/308 |
| 2010/0076238 A1 | 3/2010 | Brandvold et al. | |
| 2011/0237838 A1 | 9/2011 | Zmierczak et al. | |
| 2011/0288352 A1* | 11/2011 | Peters et al. | 585/14 |

FOREIGN PATENT DOCUMENTS

| | | | |
|---|---|---|---|
| CN | 101643666 | * | 2/2010 |
| CN | 101643666 A | | 2/2010 |
| CN | 101892079 A | | 11/2010 |
| GB | 1301019 | | 12/1972 |
| RU | 2074879 C1 | | 3/1997 |
| WO | 2010088486 A1 | | 8/2010 |

OTHER PUBLICATIONS

Jelle Wildschut; "Pyrolysis Oil Upgrading to Transportation Fuels by Catalytic Hydrotreatment"; Rijksuniversiteit Groningen; Groningen, the Netherlands; Dec. 4, 2009; pp. 1-190.
Dinesh Mohan, et al; "Pyrolysis of Wood/Biomass for Bio-Oil: A Critical Review"; Energy & Fuels; 2006; vol. 20; pp. 848-889; 2006 American Chemical Society; Published on Web Mar. 10, 2006.
Zhe Tang, et al; "One Step Bio-Oil Upgrading Through Hydrotreatment, Esterification, and Cracking"; Industrial & Engineering Chemistry Research; vol. 48; pp. 6923-6929; 2009 American Chemical Society; Published on Web Jul. 8, 2009.
George W. Huber, et al; "Synthesis of Transportation Fuels From Biomass: Chemistry, Catalysts, and Engineering"; Chemical Reviews; 2006; vol. 106; pp. 4044-4098; 2006 American Chemical Society; Published on Web Jun. 27, 2006.
Suping Zhang, et al; "Upgrading of Liquid Fuel From They Pyrolysis of Biomass"; Bioresource Technology; Mar. 2005; vol. 96; Issue 5; pp. 545-550.
Ferran De Miguel Mercader, et al; "Pyrolysis Oil Upgrading for Co-Processing in Standard Refinery Units"; University of Twente; Enschede, the Netherlands; Nov. 12, 2010; pp. 1-175.
Jelle Wildschut, et al; "Hydrotreatrnent of Fast Pyrolysis Oil Using Heterogeneous Noble-Metal Catalysts"; Industrial & Engineering Chemistry Research; 2009; vol. 48; pp. 10324-10334; 2009 American Chemical Society; Puyblished on Web Oct. 26, 2009.
Machine translation of cited reference CN101171324A.
Machine translation of cited reference CN101829079A.
Machine translation of cited reference CN101544910A.

* cited by examiner

HYDRODEOXYGENATION OF PYROLYSIS OIL IN PRESENCE OF ADMIXED ALCOHOL

SUMMARY OF THE INVENTION

The present invention relates to the hydrodeoxygenation of pyrolysis oils in the presence of an alcohol.

BACKGROUND OF THE INVENTION

There is currently a demand for fuels from sources other than hydrocarbons. One such source is pyrolysis oil. However, pyrolysis oil as a source of fuels is not without its drawbacks. For example, pyrolysis oils contain high levels of oxygenated species that are highly reactive, which makes the pyrolysis oil unstable and unfit for use.

THE INVENTION

The inventors hereof have unexpectedly discovered that by hydroprocessing pyrolysis oil at a temperature of less than 300° C. in the presence of a catalyst and at least one alcohol containing from 4 to 9 carbon atoms, a product can be produced that is suitable for blending or further processing.

Catalyst

The catalysts suitable for use herein can be selected from any bulk or supported hydroprocessing catalyst, preferably a hydrodeoxygenation catalyst. In the case of bulk catalysts, any bulk catalyst containing greater than 50 wt. % metals, based on the total weight of the catalyst, can be used herein. In some embodiments, the bulk catalysts used contain at least at least one Group VIII metal and at least one Group VIB metal, and sometimes at least one Group V metal. Supported catalysts suitable for use herein typically contain at least one Group VIII metal and at least one Group VIB metal on any one or more of silica, alumina, silica-alumina, carbon, activated carbon, MgO, TiO$_2$ and ZrO$_2$, preferably a support consisting of essentially alumina. By consisting essentially of alumina, it is meant that the support contains greater than 98 wt. % alumina, preferably greater than 99 wt. %, based on the total weight of the support. The at least one Group VIII metal is preferably selected from Fe, Co, Ni, and combinations thereof, more preferably Co, Ni, or Co and Ni, and most preferably Ni; and the at least one Group VIB metal, is preferably selected from Mo, W, or Mo and W, more preferably Mo. The at least one Group VIII metal is typically present in an amount ranging from about 0.5 to about 20 wt. %, preferably from about 2 to about 8% and more preferably about 3 to about 6 wt %. All metal weight percents of the Group VIII metals are calculated as the metal(mono)oxides. The at least one Group VIB metal will typically be present in an amount ranging from about 2 to about 50 wt. %, preferably from about 10 to about 40 wt. %, and more preferably from about 15 to about 30 wt. %. All metals weight percents of the Group VIB metals are calculated as the metal(tri)oxides. The supported catalysts used herein can also comprise at least one promoter selected from those known in the hydroprocessing catalyst art to enhance the performance of the catalyst. The supported catalysts of the present invention can contain up to about 15 wt. %, more typically up to about 10 wt. %, and more typically from about 1 to about 10 wt. %, of the promoter, calculated as the oxide. In some embodiments, the promoter is selected from silicium, boron, fluorine, potassium, or phosphorous, or a combination thereof. The promoter can be incorporated by any known methods including depositing the promoter onto the surface of the support or incorporation of the promoter into the catalyst support, or both.

Alcohol

The at least one alcohol, in some embodiments only one, suitable for use herein is selected from any alcohol containing in the range of from about 4 to about 9 carbon atoms. In preferred embodiments, the at least one alcohol is selected from those alcohols containing in the range of from about 4 to about 6 carbon atoms. In some embodiments, the at least one alcohol is isobutanol. The at least one alcohol described and used herein is in addition to any alcohol(s), or is an added alcohol(s), that may be present in the pyrolysis oil(s). The at least one alcohol may be the same as or different from any alcohol(s) present in the pyrolysis oil(s) used herein.

In some embodiments, the at least one alcohol suitable for use herein is a mixture of at least one first alcohol, preferably only one, containing in the range of from about 4 to about 9 carbon atoms, preferably about 4 to about 6 carbon atoms, and at least one second alcohol, preferably only one, containing in the range of from about 1 to about 15 carbon atoms, wherein the first and second alcohol preferably have a different number of carbon atoms. Non limiting examples of suitable second alcohols containing from about 1 to about 15 carbon atoms, include in addition to those described above, methanol, ethanol, propanol, butanol, pentanol, hexanol, heptanol, octanol, nonanol, decanoland their isomers.

Pyrolysis Oil

In the practice of the present invention, any pyrolysis oil can be used. Preferably the pyrolysis oil used herein is derived from biomass. In some embodiments, the pyrolysis oil is derived from fast pyrolysis.

Hydroprocessing Conditions

In the practice of the present invention, the pyrolysis oil and at least one alcohol contact the hydroprocessing catalyst under hydroprocessing conditions including temperatures of less than about 300° C. thereby producing at least a hydroprocessing product, which comprises at least water, at least a portion of the at least one alcohol, and products. In preferred embodiments, the temperatures are in the range of from about 40° C. to about 300° C., more preferably in the range of from about 100° C. to about 300° C., most preferably in the range of from about 160° C. to about 290° C.

The hydroprocessing conditions suitable for use herein also include pressures in the range of from about 0.1 to about 30, preferably in the range of from about 1 to about 20, more preferably in the range of from about 5 to about 15, most preferably in the range of from about 8 to about 12. All pressures in Mpa.

The hydroprocessing conditions suitable for use herein also include hydrogen treat gas rates in the range of from about 100 Nl/kg feed to about 5000 Nl/kg feed, preferably in the range of from about 400 Nl/kg feed to about 3000 Nl/kg feed, more preferably in the range of from about 600 Nl/kg feed to about 2000 Nl/kg/feed, most preferably in the range of from about 800 Nl/kg feed to about 1500 Nl/kg feed.

After hydroprocessing, the hydroprocessing product can be treated to recover at least a portion of the products contained therein. The method by which the products are recovered is not critical to the present invention, and any method or processing known to be effective at separating such products can be used. For example, the hydroprocessing product can be subjected to fractional distillation whereby at least a portion of water and at least a portion of the at least one alcohol are removed, and the products are thereby recovered. In some embodiments, at least a portion, preferably substantially all, of any water present in the hydroprocessing product is removed by phase separation or settling prior to product recovery, particularly when distillation is used for product recovery. In these embodiments, the hydroprocessing product is allowed to separate or caused to separate into at least an organic phase and an aqueous phase, and the aqueous phase is removed or the organic phase recovered. The recovered organic phase and/or the aqueous phase, can be further processed, such as by fractional distillation, to recover any products present therein.

The inventors hereof have discovered that the present invention produces useful products containing low levels of oxygenated species even though the processes of the present invention operate at such low temperatures, and preferably pressures. In some embodiments, the products produced from the present invention contain less than about 20 wt. %, based on the total weight of the product, oxygen, preferably less than about 10 wt. %, more preferably in the range of from about 4 wt % to about 10 wt. %, most preferably below about 4 wt %.

The inventors hereof have also discovered that the mild operating conditions of the present invention unexpectedly enhance the process by reducing catalyst leaching and restructuring.

In some embodiments, the present invention includes at least one second hydroprocessing stage. The conditions, catalysts, etc. of the at least one second hydroprocessing stage can be selected from any of those described above. When the at least one second stage is employed, it is preferred that the conditions of the second stage include temperatures higher than those used in the first stage.

The inventors hereof have also discovered that the present invention produces high quality, low oxygen, products, e.g. containing less than 10 wt. % oxygen, which finds use in various blending and refining operations. The inventors hereof have also discovered that the present invention converts surprisingly low quantities of the added alcohols, allowing separation and recycling of the alcohols and/or multiple process steps at increasingly severe conditions using all or part of the same alcohol. In addition, the inventors hereof have also unexpectedly discovered that alcohols can be selected to tailor-make products suitable for use in specific applications. For example, when the alcohol is isobutanol, the present invention produces isobutane that can be used in refinery gasoline alkylation processes. These alkylation processes produce an alkylate product suitable for use as an octane enhancer for, e.g., blending with hydrocarbon fractions suitable for use as fuels. By variation of the process conditions the amount of isobutane produced can be controlled. Also by variation of the process conditions the degree of deoxygenation of the products from the pyrolysis oil can be controlled.

Optional Recycling

In some embodiments, the process of the present invention includes recycling of at least a portion of the hydroprocessing product, and/or at least a portion of any hydrogen, and/or recycling of at least a portion of the alcohol removed from the hydroprocessing product, and/or recycling at least a portion of any product(s). The hydroprocessing product of the present invention comprises at least water, at least a portion of the at least one alcohol, and products, such products described above. The recycled portion of the at least one hydroprocessing product and/or at least a portion of any hydrogen, and/or at least a portion of the alcohol can be introduced to any part of the process scheme, depending on the need for such recycle and optimization of the process, such as for example a quench to manage and/or maintain a temperature. In some embodiments, the recycled portion can be i) recycled directly to the hydroprocessing reactor; ii) combined or mixed with the feed to the hydroprocessing reactor; iii) recycled to a heat exchanger to recover the heat value therefrom; iv) or separated or divided and introduced to any combination of i)-iv). If the process of the present invention utilizes more than one hydroprocessing stage, e.g. at least one second hydroprocessing stage, the recycled portion of the at least one hydroprocessing product can be directed to any of the hydroprocessing stages, or divided or separated with at least a portion introduced separately to each such hydroprocessing stage, or any combination of i)-iv) above.

In some embodiments, at least a portion of the hydroprocessing product is recycled without further processing. In these embodiments, the amount of hydroprocessing product recycled will vary, based on optimization of the process. In some embodiments in the range of from about 1 wt. % to about 98 wt. %, based on the total weight of the hydroprocessing product, of the hydroprocessing product is recycled; in some embodiments in the range of from about 10 wt. % to about 94 wt. %; in some embodiments in the range of from about 50 wt. % to about 84 wt. %, all on the same basis.

In other embodiments, at least a portion of the water is removed from the hydroprocessing product thereby producing a lower water hydroprocessing product, and at least a portion of the lower water hydroprocessing product is recycled. In these embodiments, the lower water hydroprocessing product that is recycled contains in the in the range of from about 1 wt. % to about 30 wt. % water, based on the total weight of the lower water hydroprocessing product; in some embodiments in the range of from about 4 wt. % to about 20 wt. %; in some embodiments in the range of from about 7 wt. % to about 15 wt. %, all on the same basis. In these embodiments, the amount of the lower water hydrproccessing product recycled will vary, based on optimization of the process. In some embodiments in the range of from about 1 wt. % to about 98 wt. %, based on the total weight of the lower water hydroprocessing product, of the lower water hydroprocessing product is recycled; in some embodiments in the range of from about 10 wt. % to about 94 wt. %; in some embodiments in the range of from about 50 wt. % to about 84 wt. %, all on the same basis. The recycled portion of the lower water hydroprocessing product can be treated in the same manner as the recycled portion of the hydroprocessing product, described above.

In other embodiments, at least a portion of the at least one alcohol and at least a portion of the water present in the hydroprocessing product are removed thereby producing a lower water and lower at least one alcohol hydroprocessing product, and at least a portion of the so produced lower water and lower at least one alcohol hydroprocessing product is recycled. In these embodiments, the at least a portion of the so produced lower water and lower at least one alcohol hydroprocessing product that is recycled contains in the range of from about 1) wt. % to about 30) wt. % water, based on the total weight of the lower water hydroprocessing product; in some embodiments in the range of from about 4) wt. % to about 20) wt. % water; in some embodiments in the range of from about 7) wt. % to about 15) wt. % water, all on the same basis; and in the range of from about 5) wt. % to about 60) wt. % of the at least one alcohol, based on the total weight of the lower water and lower at least one alcohol hydroprocessing product; in some embodiments in the range of from about 10) wt. % to about 50) wt. % of the at least one alcohol; in some embodiments in the range of from about 20) wt. % to about 35) wt. % of the at least one alcohol, all on the same basis. In these embodiments, the amount of the lower water and lower at least one alcohol hydroprocessing product recycled will vary, based on optimization of the process. In some embodiments in the range of from about 1) wt. % to about 98) wt. %, based on the total weight of the lower water and lower at least one alcohol hydroprocessing product, of the lower water and lower at least one alcohol hydroprocessing product is recycled; in some embodiments in the range of from about 10) wt. % to about 94) wt. %; in some embodiments in the range of from about 50) wt. % to about 84) wt. %, all on the same basis. The recycled portion of the lower water and lower at least one alcohol hydroprocessing product can be treated in the same manner as the recycled portion of the hydroprocessing product, described above.

The method by which at least a portion of the water, at least a portion of the at least one alcohol, or combinations thereof, is removed from the hydroprocessing product is not critical to the instant invention. Non-limiting examples of suitable methods include settling, decanting, distillation, or the like. In some embodiments, settling or decanting or distillation, or any combination thereof is used.

The above description is directed to several embodiments of the present invention. Those skilled in the art will recognize that other means, which are equally effective, could be devised for carrying out the spirit of this invention. It should also be noted that preferred embodiments of the present invention contemplate that all ranges discussed herein include ranges from any lower amount to any higher amount. For example, when discussing the hydroprocessing conditions temperatures in the range of from about 40° C. to about 160° C., in the range of from about 100° C. to about 160° C., in the range of from about 100° C. to about 190° C., etc. are within the scope of the present invention.

The following examples will illustrate the present invention, but are not meant to be limiting in any manner.

EXAMPLES

The following examples used a test unit with several liquid feed supply vessels, a liquid and hydrogen dosing system, a down flow operated fixed bed reactor using a furnace with 3 heating zones and a gas-liquid separation and sampling system for gas and liquid products.

The fixed bed reactor had an internal diameter of about 8.5 mm and a length of about 60 cm. The thermowell had an external diameter of about 1.6 mm. The reactor was loaded from top to bottom by, about 5 cm of SiC 16 mesh, about 49 cm non-diluted catalyst and about 6 cm of SiC 16 mesh. The pyrolysis oil feed used in the following examples had the properties outlined in Table 1 below. Catalyst A is a supported catalyst containing 4 wt. % NiO and 25 wt. % $MoO_3$, and 7 wt. % $P_2O_5$ with the remainder of the catalyst being alumina carrier. Catalyst B is a bulk metaloxide catalyst formed according to the recipe and procedure of Example 6 of U.S. Pat. No. 6,162,350, specifically identified as Sample 18357-109 therein.

TABLE 1

|  | % H2O | % C | % H | % O | density 15C [g/ml] |
|---|---|---|---|---|---|
| Pyrolysis oil | 22.7 | 42.7 | 7.6 | 49.2 | 1.22 |
| iBuOH |  |  |  |  | 0.804 |
| EtOH |  |  |  |  | 0.789 |

Before use, each catalyst was separately activated by the following procedure:

Catalyst Activation:

For catalyst activation a DMDS spiked (2.5 wt % S) diesel feed was used. The feed was first introduced at the following conditions:

| $H_2$/feed | 300 Nl/kg |
| LHSV | 2 |
| Pressure | 4.5 MPa |
| Temperature (° C.) | 30 |

Thereafter, the temperature of all furnace sections was increased according to the following temperature program keeping the other conditions the same:

| Temperature (° C.) ramp1 | 30→ 250, 10° C./uur |
| Temperature dwell (° C.) | 10.5 hours |
| Temperature (° C.) ramp2 | 250→ 320, 5° C./uur |
| Temperature dwell (° C.) | 2 hours |
| Cooling down to room temperature | |

Test Procedures:

First isobutanol (DMDS spiked, 5000 ppm S on weight basis) was introduced at LHSV 2 and $H_2$/feed 300 Nl/kg. Pressure was 10 Mpa. During the introduction period of 2 hours the temperature of the bottom and middle section of the furnace was increased from about room temperature to 100° C. Thereafter, LHSV was reduced to 0.5 and H2/feed set to the $H_2$/feed of the first condition and over a time period of about 4 hours the reactor temperature was increased to 150° C. (bottom and middle section of furnace). Then LHSV was changed to the desired LHSV of the first test condition and also the hydrogen flow was set to the desired value of the first test condition. LHSV is always based on total liquid feed to the reactor. Thereafter, the feed was switched from isobutanol to the pyrolysis oil/isobutanol (DMDS spiked, 5000 ppm on weight basis) mixture. Next the temperature of the bottom section of the furnace was increased from 150° C. to the desired bottom temperature with a temperature ramp of 20° C./h. After 20 hours stabilization, sampling was started.

Analytical Methods

GC-methods were used to measure the composition of the off-gas and to determine the isobutanol concentration in the various feeds and products. The Karl-Fisher method was used to determine the water concentration in the various feeds and products. The C- H- N- and O-content of the various feeds and products was determined by an organic elemental analyzer (Interscienze, Flash 2000). FT-IR (Thermo Scientific Nicolet iS-10 Mid Infrared) and GC×GC methods (HP6890) were used for further characterization of the feed and products.

Definitions

Total feed: Feed with water and alcohol diluent (iBuOH or EtOH)
Dry feed: Feed without water and without diluent
Dry oil: Product without water and without diluent $$Yield_{dry.oil} = \frac{\phi_{dry.oil}}{\phi_{dryfeed}} \cdot 100\%$$

Dry oil yield $$Yield_{water} = \frac{\phi_{water.OUT} - \phi_{water.IN}}{\phi_{dryfeed}} \cdot 100\% [\% \text{ weight}]$$

Water yield $$Yield_{gas} = \frac{\phi_{gas.analyzers} - \phi_{H2}}{\phi_{dryfeed}} \cdot 100\% \; [\% \text{ weight}]$$

Gas yield:
Weight flow $\phi$=g/h
O content: O content corrected for O in water and O in diluent
C content: C content corrected for C in diluent
H content: H content corrected for H in water and H in diluent
Density calculation of dry oil in two steps:

$$\rho_{organic} = \rho_{product} - \frac{\% \, iBuOH \cdot \rho_{iBuOH}}{(100\% - \% \, iBuOH)}$$

Step 1:

$$\rho_{dry.oil} = \rho_{organic} - \frac{\% \, H_2O \cdot \rho_{H_2O}}{(100\% - \% \, H_2O)}$$

Step 2:

Example 1

Figure 1:
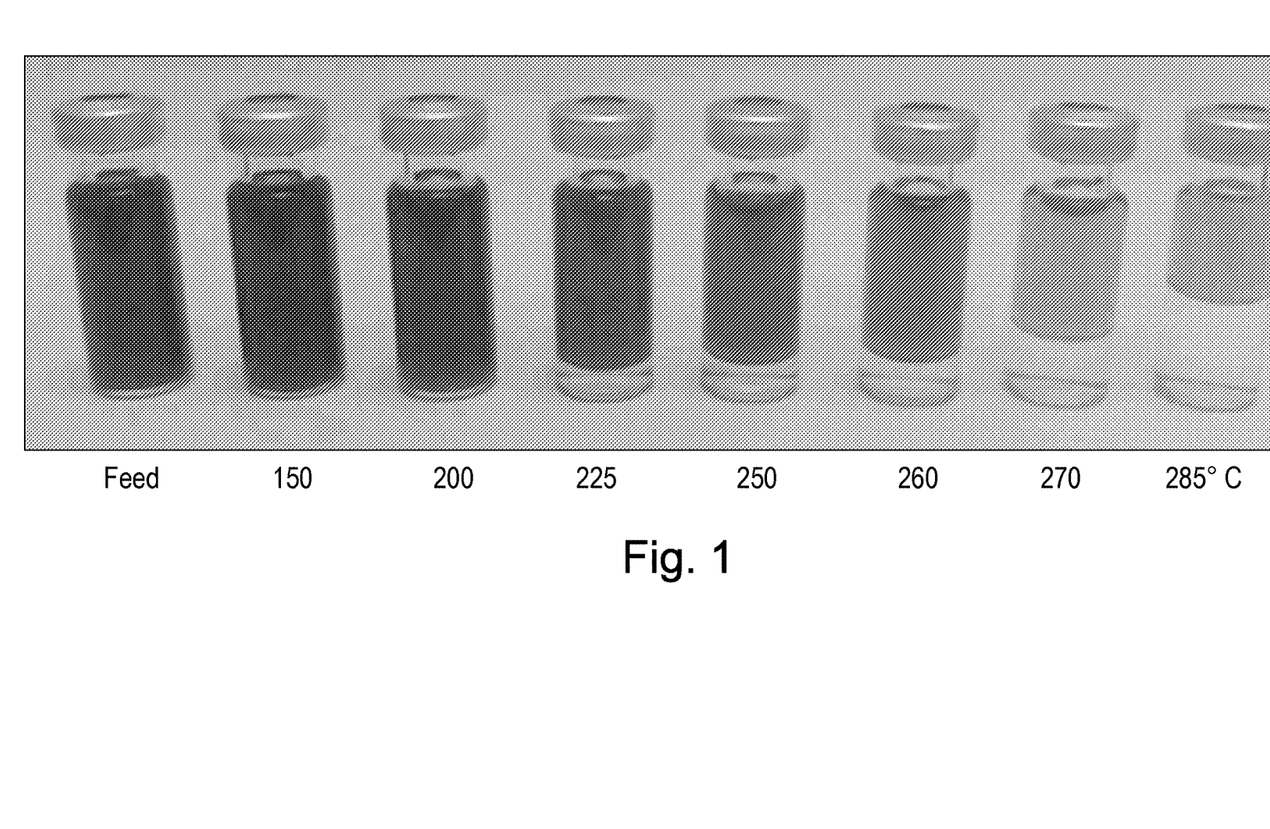
FIG. 1 provides pictures of samples of the liquid products obtained at various reactor bottom temperatures and the feed for Example 1.

Catalyst B was evaluated at various bottom temperatures with a mixture of 50% pyoil and 50% isobutanol to investigate the influence of temperature on conversion to various products. LHSV=0.25; H2/feed=2000 Nl/kg; Pressure=10 MPa In FIG. 1 samples of the liquid products obtained at various reactor bottom temperatures are shown. It can be observed that above an outlet temperature of about 200-225° C. the liquid products started to separate in two distinct layers. One layer comprising mainly water, some isobutanol and a minor amount of organic compounds (measured using GC-MS) and the other layer comprising mainly the product oil and isobutanol. The density ("D") and oxygen ("O") content of the dry product oil (without water and isobutanol) were calculated from the values measured on the product oil/isobutanol mixture as such, see Table 2.

The composition of the oil products was investigated by FT-IR and GC×GC methods. The results are presented in FIGS. 2 to 5.

Figure 2:
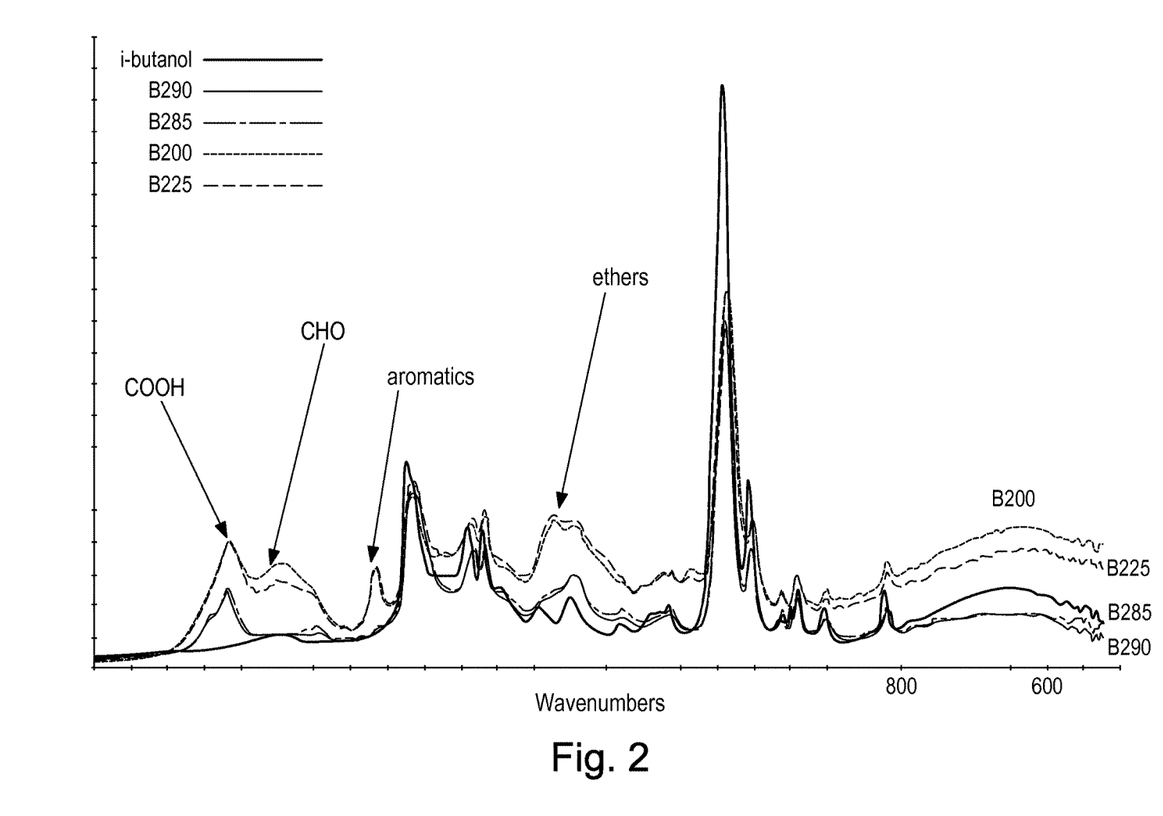
FIG. 2 provides FT-IR measurements from the Examples.

It can be seen from the FT-IR results in FIG. 2, that the intensity of the peaks belonging to aromatic compounds and oxygen functional groups is reduced to various lower levels depending on the reactor bottom temperature (e.g. B200 indicates 200° C. reactor bottom temperature and B290 in a similar way 290° C.). For reference the FT-IR spectrum of isobutanol (i-butanol) is plotted in the same figure.

Figure 3:
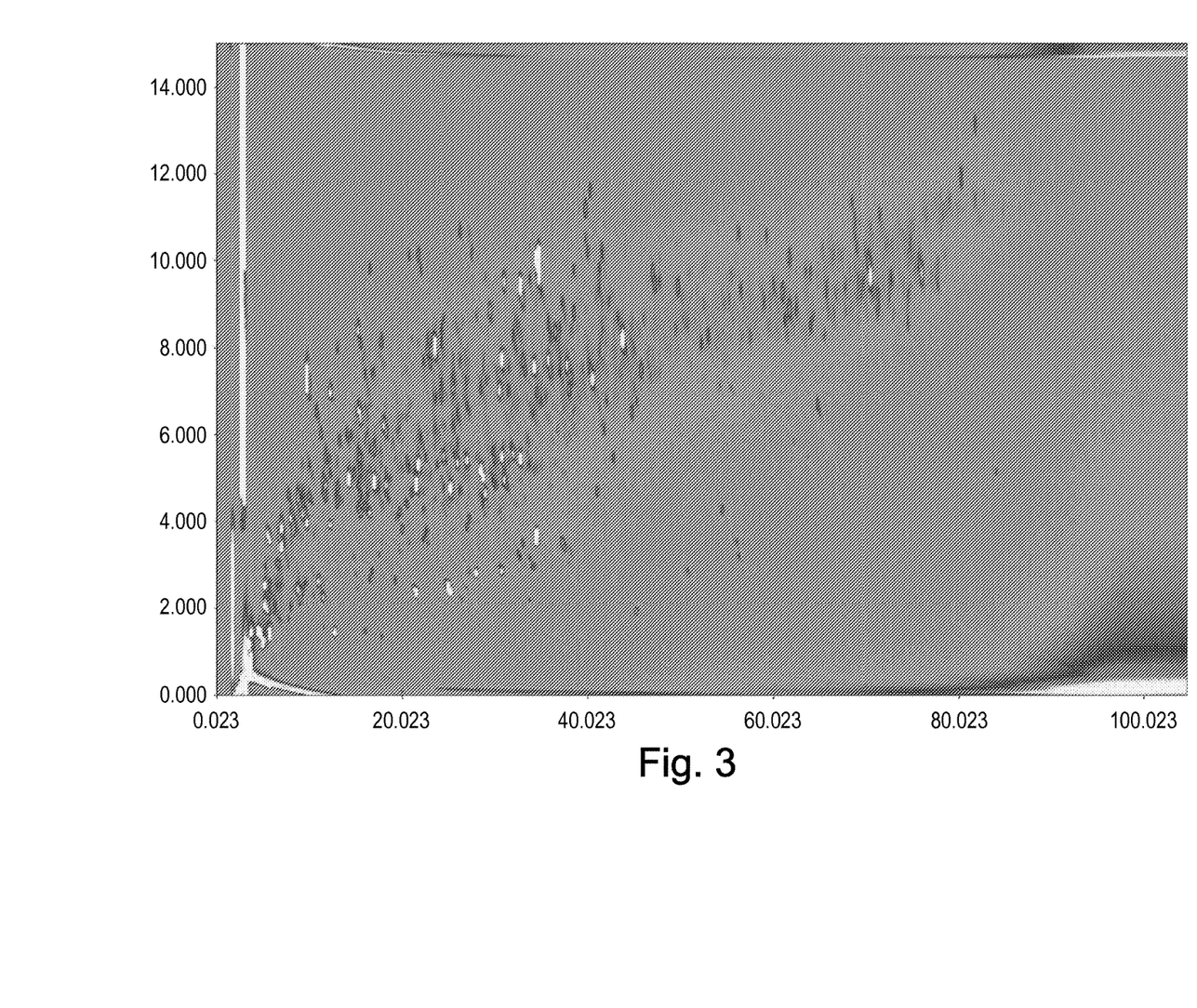
FIG. 3 provides GC×GC results of the feed from the Examples.

From GC×GC (FIGS. 3-5) it can be observed by those skilled in the art that the products become less polar and more saturated with increasing temperatures. At the highest temperatures mainly so called fungible (can be mixed with crude oil derived products) paraffins and naphtenes remain. In FIG. 3 the results obtained with the feed are shown. Coordinates Y and X are indicating resp. higher polarity and higher molecular weight of the fractions that were separated by the GC×GC method. The feed contains relatively polar (e.g. oxygenated compounds, polyaromatic compounds) and heavy components.

Figure 4:
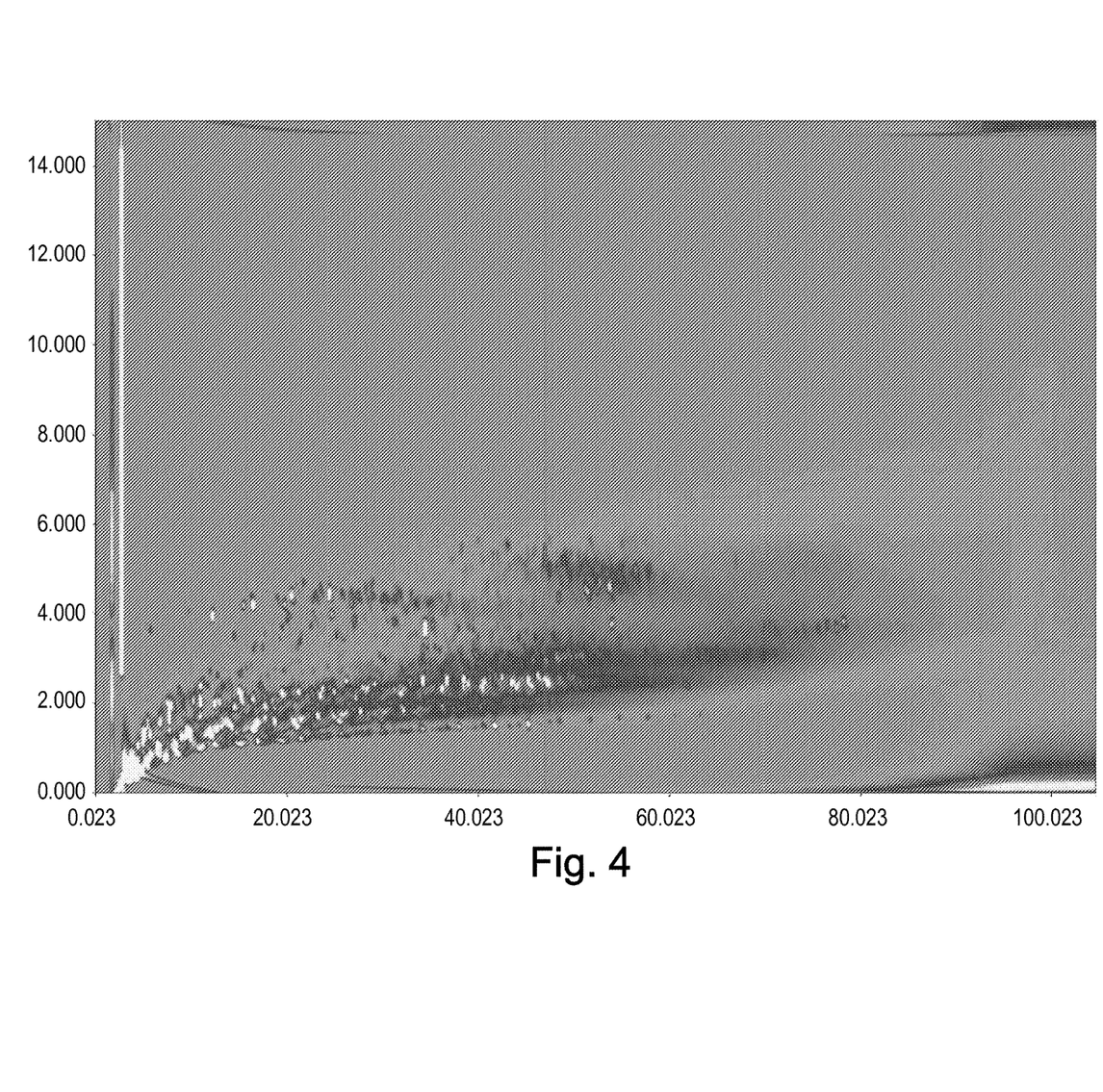
FIG. 4 provides GC×GC results of the product at 285° C. from the Examples.
Figure 5:
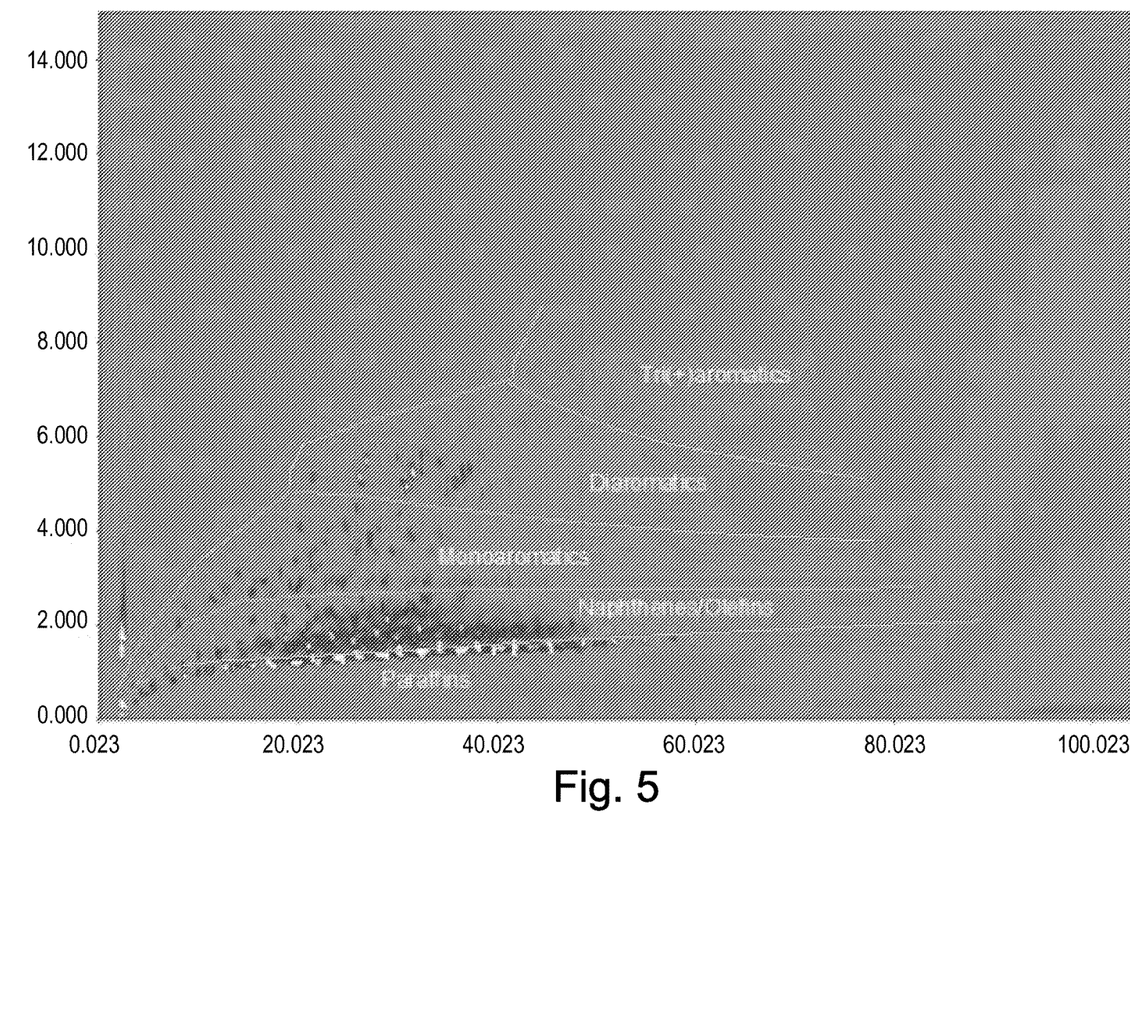
FIG. 5 provides GC×GC for gasoil derived from crude oil for reference.

From FIG. 4 it can be seen that the components of the product oil of the invention are much less polar (deoxygenated, hydrogenated) and also somewhat lighter than the components of the feed. For reference FIG. 5 is presented which shows where the components of gasoil derived from crude oil (almost no oxygenated compounds) can be observed by the GC×GC method used. From FIGS. 4 and 5 it can be observed that the products of the invention would be mainly naphtenic, paraffinic and monoaromatic compounds.

Figure 6:
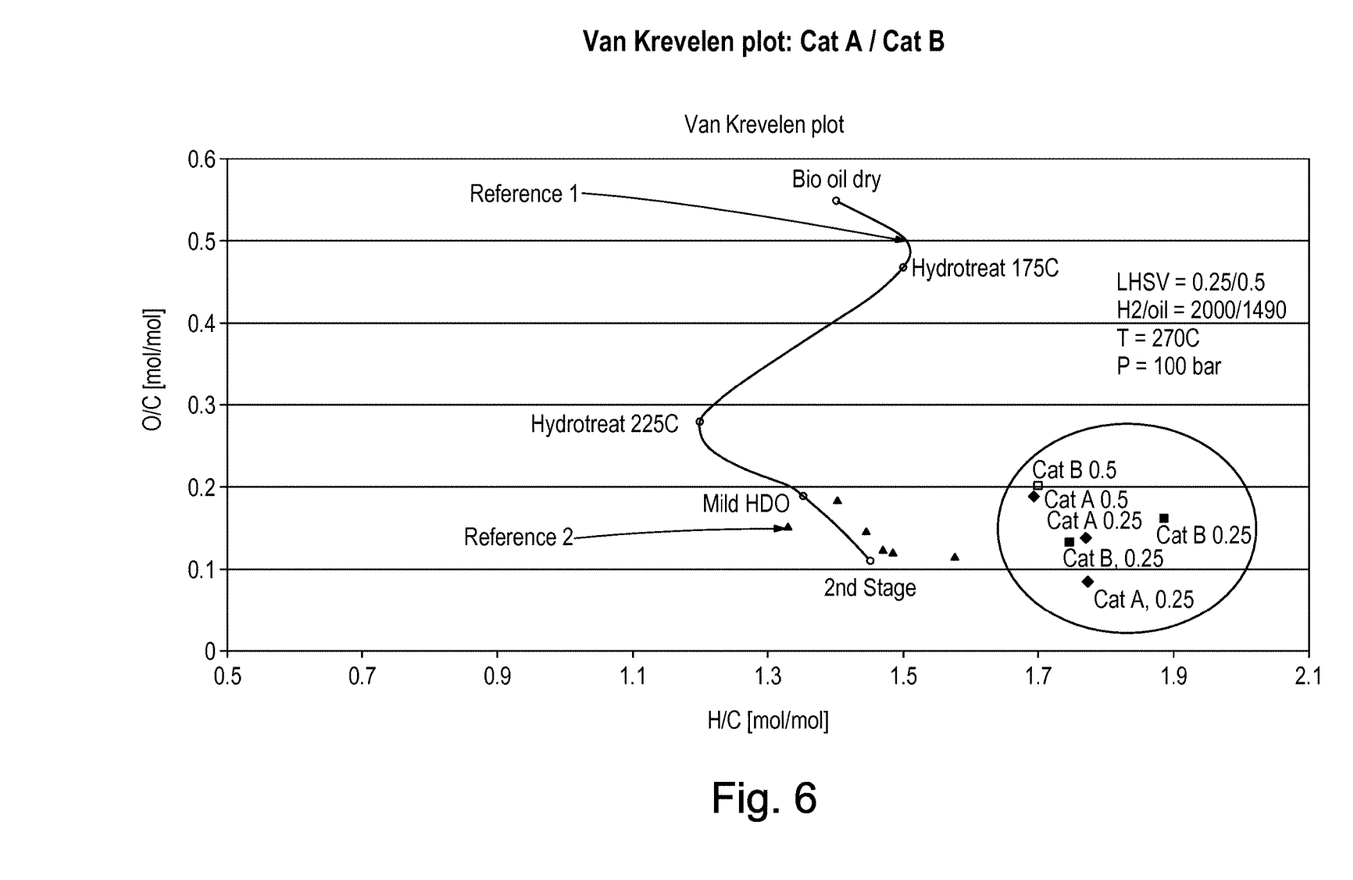
FIG. 6 provides a "van Krevelen" plot that compares the molar O/C ratio of the dry oil (illustrating the deoxygenation level) with the molar H/C ratio of the dry oil (illustrating the hydrogenation level) from the Examples.

In combination with FT-IR results (reduced aromatic compound peak) it can be concluded that the aromatic compounds have been hydrogenated for a large part and consequently mainly naphtenic and paraffinic compounds remain. This is further supported by the relatively high H/C molar ratio of the dry oil (see FIG. 6).

Example 2

Catalyst A and B were evaluated at various conditions to investigate the effect of catalyst type (with and without carrier).
Conditions
Feed: Mixture of 50/50 vol % Pyrolysis oil/Isobutanol
LHSV: 0.25 and 0.5
H2/feed: 2000 and 1490 Nl/kg
Pressure: 10 MPa
Temperature: 270° C. bottom The results presented in the tables below are representative for a run time of about 48-96 hours. With both catalysts a similar two layer system was observed as described in

TABLE 2

| | | | | Temp (° C.) | | | | |
|---|---|---|---|---|---|---|---|---|
| | Feed | 150 | 200 | 225 | 250 | 260 | 270 | 285 |
| $D_{(as\,such)}$ (g/ml) | 1.01 | 0.94 | 0.94 | 0.93 | 0.90 | 0.87 | 0.87 | 0.83 |
| $D_{(no\,iBuOH\,no\,H2O)}$ (g/ml) | 1.28 | | 1.10 | 1.05 | 0.97 | | 0.93 | 0.85 |
| O (dry oil) wt. % | 37.6 | | 23.2 | 20.3 | 13.5 | | 12.7 | 6.2 |

It can be observed in Table 2 that depending on the reactor bottom temperature the oxygen content of the dry product oil is reduced. Levels significantly below 10 wt % oxygen are obtained at a relatively low temperature and pressure of respectively 285° C. and 10 MPa.

Example 1. Oxygen content is reduced to about 14% at these very mild conditions. Yields of dry oil are relatively high and it can be seen that oxygen is removed from the dry oil and converted to $H_2O$ and $CO_2$. Next to that some CO and light hydrocarbon gases are formed.

TABLE 3

O-content and product yields

|  | LHSV | H$_2$/feed | O [wt %] | O/C [mol/mol] | H/C [mol/mol] | yields [% dry feed] dry oil | water | gas |
|---|---|---|---|---|---|---|---|---|
| Cat A, | 0.25 | 2000 | 14% | 0.14 | 1.77 | 55% | 17% | 28% |
| Cat A, | 0.5 | 1490 | 18% | 0.19 | 1.69 | 69% | 13% | 18% |
| Cat B, Bulk metal | 0.25 | 2000 | 15% | 0.16 | 1.88 | 58% | 17% | 25% |
| Cat B, Bulk metal | 0.5 | 1490 | 19% | 0.20 | 1.70 | 71% | 12% | 17% |

TABLE 4

Gas yields

|  | LHSV | gas | iC$_4$ | C$_2$ | CH$_4$ | CO | CO$_2$ | Other* | sum |
|---|---|---|---|---|---|---|---|---|---|
|  |  | Yields, % of total feed |  |  |  |  |  |  |  |
| Cat A, | 0.25 | 17.2% | 5.8% | 1.7% | 2.1% | 0.4% | 2.5% | 4.7% | 17.2% |
| Cat A, | 0.5 | 8.8% | 1.4% | 1.0% | 1.4% | 0.3% | 1.7% | 3.0% | 8.8% |
| Cat B, Bulk metal | 0.25 | 15.6% | 5.6% | 1.7% | 2.0% | 0.3% | 1.9% | 4.1% | 15.6% |
| Cat B, Bulk metal | 0.5 | 9.9% | 1.7% | 1.3% | 1.7% | 0.3% | 1.5% | 3.5% | 9.9% |

*Other: H$_2$O, C$_3$, nC$_4$, C$_{6+}$, iC$_5$, nC$_5$

The results can be further represented by a "van Krevelen" plot (FIG. 6), which compares the molar O/C ratio of the dry oil (illustrating the deoxygenation level) with the molar H/C ratio of the dry oil (illustrating the hydrogenation level). Next to the results obtained with the methods of the invention are prior art results (Reference 1: Venderbosch R. H. et al, J Chem Technol Biotechnol 2010, 85, p. 674-686) (Reference 2: Elliott D. C., Energy Fuels 2007, 21(3), p. 1792-1815) plotted to illustrate that the examples according to the present invention provide surprisingly high deoxygenation and hydrogenation level of the products compared to prior art technology. From the results in the tables it can also be concluded that relatively low quantities of isobutanol are converted to isobutane, e.g. in the case of the highest LHSV only about 1.4 wt % of the total feed is converted to iC$_4$ with catalyst A and 1.7 wt % in the case of catalyst B. Maximum conversion of the feed to iC$_4$ is 5.8 wt %. Also the differences between the two catalysts are very small, and both bulk catalysts and supported catalysts provide for nearly equivalent results.

Example 3

The use of ethanol instead of isobutanol was investigated and the results were compared.
Conditions
Catalyst: Cat A
Feed: Mixture of 50/50 vol % Pyrolysis oil/Ethanol
LHSV: 0.25
H2/oil: 2000 Nl/kg
Pressure: 10 Mpa
Temperature: 270° C. bottom See for further details Example 2. All procedures of Example 2 are the same except for the feed used, which is a mixture of 50/50 vol % Pyrolysis oil/Ethanol.

The results presented in Tables 5 and 6 below are representative for a run time of about 48-96 hours. In the case of ethanol the liquid product was less clear and contained 3 layers. One oil layer on top of a mainly water and ethanol containing middle layer and a heavier bottom oil layer. For the calculations the two oil layers were combined.

TABLE 5

O-content and product yields

|  | LHSV | O cont. [wt %] | O/C [mol/mol] | H/C [mol/mol] | yields [% dry feed] dry oil | water | gas |
|---|---|---|---|---|---|---|---|
| iBuOH | 0.25 | 14% | 0.14 | 1.77 | 55% | 17% | 28% |
| EtOH | 0.25 | 19% | 0.21 | 1.70 | 63% | 11% | 26% |

TABLE 6

Gas yields

|  | LHSV | gas | iC$_4$ | C$_2$ | CH$_4$ | CO | CO$_2$ | Other* | sum |
|---|---|---|---|---|---|---|---|---|---|
|  |  | Yields, % of total feed |  |  |  |  |  |  |  |
| iBuOH | 0.25 | 17.2% | 5.8% | 1.7% | 2.1% | 0.4% | 2.5% | 4.7% | 17.2% |
| EtOH | 0.25 | 22.9% | 0.0% | 11.4% | 2.1% | 0.9% | 3.0% | 5.5% | 22.9% |

*Other: H$_2$O, C$_3$, nC$_4$, C$_{6+}$, iC$_5$, nC$_5$

Figure 7:
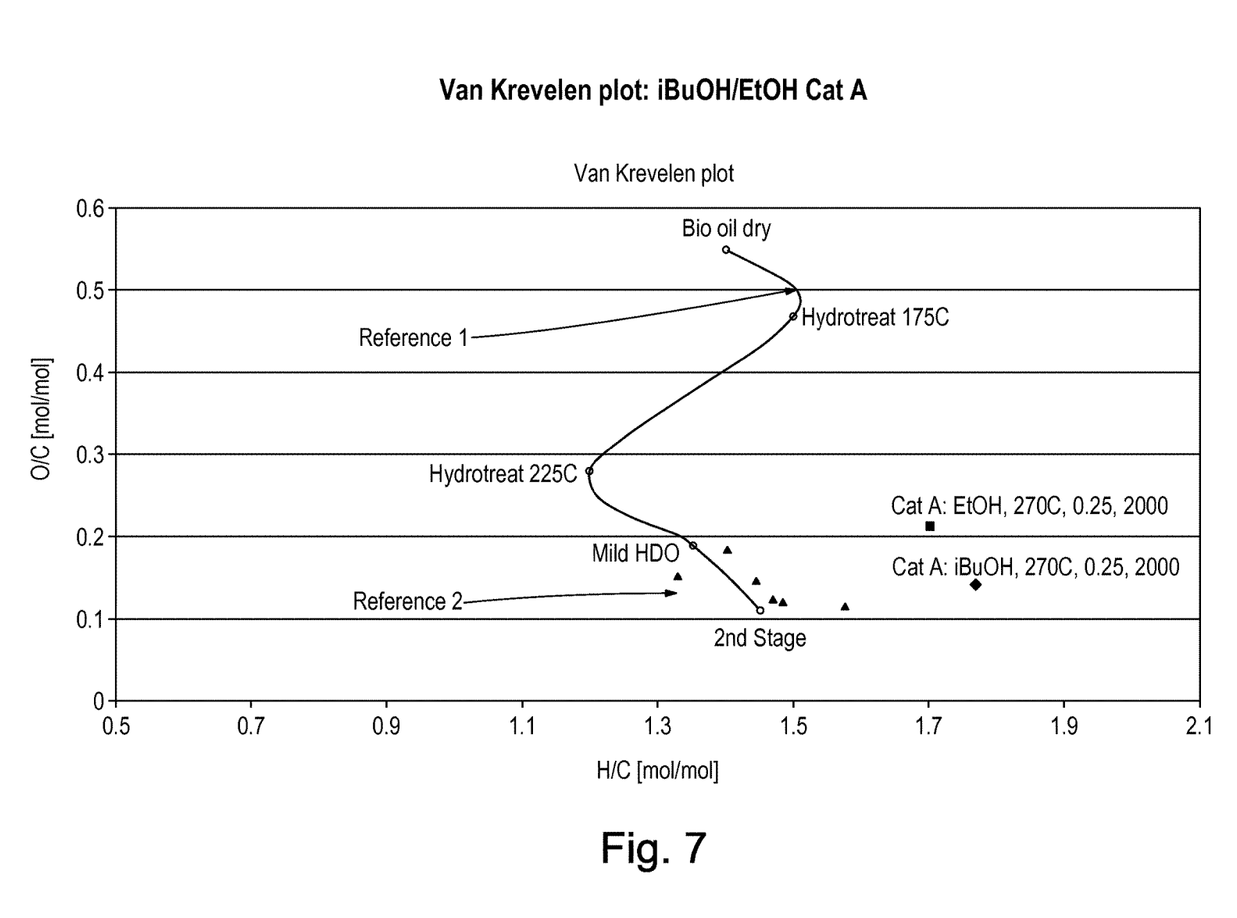
FIG. 7 provides a van Krevelen plot for comparative Example 3.

By reference to FIG. 7, it can be observed that in the case of ethanol more oxygen remains in the products at the same reaction conditions. Also the formation of gas is higher in the case of ethanol. Especially, ethane formation is higher than isobutane formation. So much more ethanol is converted than isobutanol. Altogether, surprisingly low conversion of isobutanol compared to ethanol was observed in case of this invention (see also FIG. 8).

Figure 8:
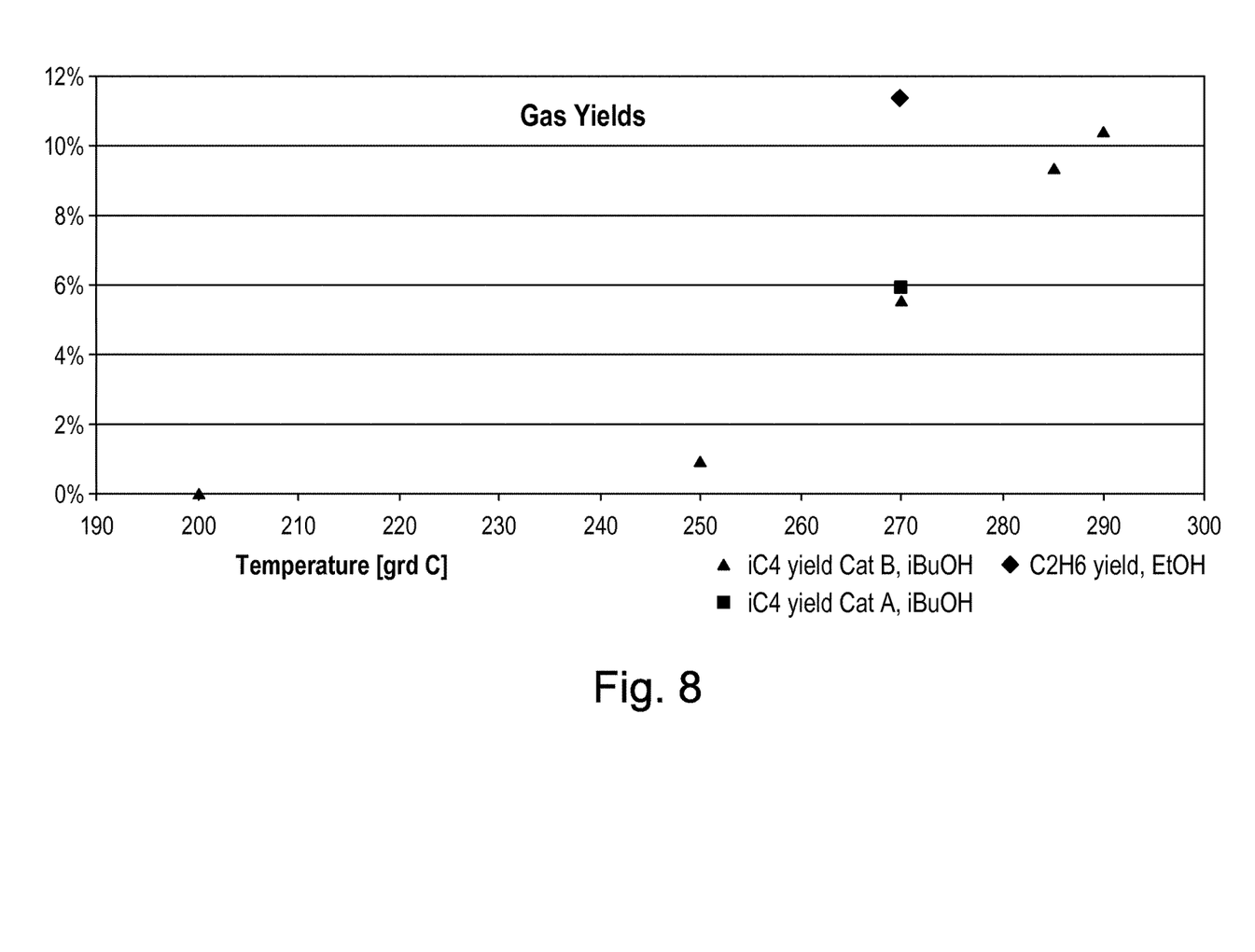
FIG. 8 provides the wt % yields of iC$_4$ (in case of dilution with iBuOH) and C$_2$H$_6$ (in case of dilution with EtOH) presented as a function of the reactor outlet temperature.

In FIG. 8 the wt % yields of $iC_4$ (in case of dilution with iBuOH) and $C_2H_6$ (in case of dilution with EtOH) are presented as a function of the reactor outlet temperature. It can be seen that the formation of the relatively low value product ethane is about two times higher than the formation of the relatively higher value product isobutane (On molar basis nearly 4 times more $C_2H_6$ is formed).

What is claimed:

1. A process comprising contacting a bulk or supported hydroprocessing catalyst with pyrolysis oil and hydrogen at temperatures lower than 290° C. in the presence of at least one added alcohol, wherein said hydroprocessing catalyst contains at least one Group VIII metal and at least one Group VIB metal and wherein said at least one added alcohol is selected from i) an alcohol containing from 4 to 9 carbon atoms, or ii) a mixture of at least one first and at least one second alcohol having the same or a different number of carbon atoms wherein said at least one first alcohol contains from 4 to 9 atoms and said at least one second alcohol contains in the range of from 1 to about 15 carbon atoms.

2. The process according to claim 1 wherein said supported catalysts comprise a support selected from silica, alumina, or silica-alumina, carbon, activated carbon, MgO, $TiO_2$ and $ZrO_2$ support.

3. The process according to claim 1 wherein said supported catalysts comprise a support consisting essentially of alumina.

4. The process according to claim 1 wherein said supported catalyst further comprises at least one promoter and/or said bulk catalyst further comprises a Group V metal component.

5. The process according to claim 1 wherein said supported catalyst comprises at least one Group VIII metal present in an amount ranging from about 0.5 to about 20 wt. % and at least one Group VIB metal present in an amount ranging from about 2 to about 50 wt. %.

6. The process according to claim 1 wherein said at least one added alcohol is isobutanol.

7. A process comprising:
a) contacting a bulk or supported hydroprocessing catalyst with pyrolysis oil and hydrogen at temperatures in the range of from about 40° C. to about 290° C. in the presence of at least one added alcohol thereby producing at least a hydroprocessing product, which comprises at least water, at least a portion of the at least one added alcohol, and products;
b) recovering at least a portion of said products from said hydroprocessing product, and
c) recycling i) at least a portion of the hydroprocessing product, ii) at least a portion of any hydrogen, iii) at least a portion of the at least one added alcohol, iv) at least a portion of the products, or v) any combination of i)-iv),
wherein said hydroprocessing catalyst contains at least one Group VIII metal and at least one Group VIB metal, and wherein said at least one added alcohol is selected from i) at least one alcohol containing from 4 to 9 carbon atoms, or ii) a mixture of at least one first and at least one second alcohol having the same or a different number of carbon atoms wherein said at least one first alcohol contains from 4 to 9 carbon atoms and said at least one second alcohol contains in the range of from about 1 to about 15 carbon atoms.

8. The process according to claim 7 wherein said hydroprocessing catalyst is selected from supported hydroprocessing catalysts containing in the range of from about 0.5 to about 20 wt. % of said at least one Group VIII metal and in the range of from about 2 to about 50 wt. % of said at least one Group VIB metal, wherein said at least one Group VIII metal is selected from Fe, Co, Ni, and combinations thereof, and said at least one Group VIB metal is selected from Mo, W and combinations thereof.

9. The process according to claim 8 wherein said supported catalysts comprise a support selected from silica, alumina, or silica-alumina, carbon, activated carbon, MgO, $TiO_2$ and $ZrO_2$ support.

10. A process comprising:
a) contacting a bulk or supported hydroprocessing catalyst with pyrolysis oil and hydrogen at temperatures in the range of from about 40° C. to about 290° C. in the presence of at least one added alcohol thereby producing at least a hydroprocessing product, which comprises at least water, at least a portion of the at least one added alcohol, and products;
b) recovering at least a portion of said products from said hydroprocessing product, and
c) recycling i) at least a portion of the hydroprocessing product, ii) at least a portion of any hydrogen, iii) at least a portion of the at least one added alcohol, iv) at least a portion of the products, or v) any combination of i)-iv),
wherein said hydroprocessing catalyst contains in the range of from about 0.5 to about 20 wt. % of said at least one Group VIII metal and in the range of from about 2 to about 50 wt. % of said at least one Group VIB metal, wherein said at least one Group VIII metal is selected from Fe, Co, Ni, and combinations thereof, and said at least one Group VIB metal is selected from Mo, W, and combinations thereof and said support is selected from silica, alumina, or silica-alumina, carbon activated carbon, MgO, $TiO_2$ and $ZrO_2$ support, and wherein said at least one added alcohol is selected from i) at least one alcohol containing from 4 to 9 carbon atoms, or ii) a mixture of at least one first and at least one second alcohol having the same or a different number of carbon atoms wherein said at least one first alcohol contains from 4 to 9 carbon atoms and said at least one second alcohol contains in the range of from about 1 to about 15 carbon atoms.

11. The process according to claim 10 wherein said supported catalysts comprise a support consisting essentially of alumina.

12. The process according to claim 10 wherein said supported catalyst further comprises at least one promoter selected from F, K, Si, B, P, or combinations thereof, wherein said at least one promoter is deposited on the surface of the support, present within the catalyst support, or both.

13. The process according to claim 10 wherein said process comprises a first hydroprocessing stage of steps a) through c) and at least one additional hydroprocessing stage wherein the temperatures of said additional hydroprocessing stage are higher than those used in the first hydroprocessing stage.

* * * * *